United States Patent [19]
Berndt et al.

[11] Patent Number: 5,518,923
[45] Date of Patent: May 21, 1996

[54] COMPACT BLOOD CULTURE APPARATUS

[75] Inventors: Klaus W. Berndt, Stewartstown, Pa.; Daniel L. Schwarz, Abingdon, Md.

[73] Assignee: Becton Dickinson and Company, Franklin Lakes, N.J.

[21] Appl. No.: 470,288

[22] Filed: Jun. 6, 1995

[51] Int. Cl.⁶ ..................................................... C12M 1/34
[52] U.S. Cl. ..................... 435/287.3; 435/801; 435/808; 435/809; 435/287.9; 435/288.7; 422/64; 422/82.08; 356/39; 356/319; 356/417; 356/440
[58] Field of Search .................................. 422/64, 82.08; 435/286, 291, 312, 801, 808, 809; 356/39, 73, 319, 417, 440

[56] References Cited

U.S. PATENT DOCUMENTS

| | | | |
|---|---|---|---|
| 4,118,280 | 10/1978 | Charles et al. | 195/127 |
| 5,093,266 | 3/1992 | Leader et al. | 436/68 |
| 5,217,876 | 6/1993 | Turner et al. | 435/34 |
| 5,432,061 | 7/1995 | Berndt et al. | 435/34 |
| 5,441,873 | 8/1995 | Knight et al. | 435/34 |

*Primary Examiner*—David A. Redding
*Attorney, Agent, or Firm*—Alan W. Fiedler

[57] ABSTRACT

The present invention describes an apparatus for detecting biological activities in a large number of blood culture containers. The containers are placed in a plurality of wells arranged in concentric rows on a turntable that is rotated about a central axis. Each well is designed to receive and hold one of a plurality of sealable containers inserted base first, with each container having optical sensing means for sensing microorganisms therein and a bar code pattern attached thereto for identification purposes. Each well has an opening in its base to allow a sensor station to monitor a fluorescence chemical sensor in each container to determine whether there is microorganism growth within the container. Prior to inserting each container into a well on the turntable, a culture medium and blood specimen are introduced into the container and the bar code is scanned to identify the container. As the containers are rotated on the turntable they are exposed to conditions enabling a variety of metabolic, physical, and chemical changes to take place in the presence of microorganisms within the specimen. The apparatus also includes a door on the front that opens and permits the turntable to be loaded and unloaded from the front of the apparatus with simultaneous access to all containers.

8 Claims, 5 Drawing Sheets

COMPACT BLOOD CULTURE APPARATUS

BACKGROUND OF THE INVENTION

1. Field of the Invention

The present invention relates to a non-invasive apparatus for detecting biological activities in a specimen such as blood. The apparatus includes a turntable having a plurality of concentric wells for receiving, holding and rotating a plurality of sealable containers. As the containers are rotated on the turntable they are exposed to conditions enabling a variety of metabolic, physical, and chemical changes to take place in the presence of microorganisms within the specimen and rotated by one or more sensor stations that monitor microorganism growth within the specimen.

2. Background Description

The presence of biologically active agents such as bacteria in a patient's body fluid, especially blood, is generally determined using blood culture containers. A small quantity of blood is injected through an enclosing rubber septum into a sterile container containing a culture medium, and the container is then incubated at 37° C. and monitored for microorganism growth.

One of the techniques used to detect the presence of microorganisms includes visual inspection. Generally, visual inspection involves monitoring the turbidity or eventual color changes of the liquid suspension of blood and culture medium. Known instrumental methods detect changes in the carbon dioxide content of the culture bottles, which is a metabolic by-product of the bacterial growth. Monitoring the carbon dioxide content can be accomplished by methods well established in the art, such as radiochemical or infrared absorption at a carbon dioxide spectral line. Until now, these methods have required invasive procedures which result in the well-known problem of cross-contamination between different containers. It has also been proposed to detect microorganism growth in sealable containers by monitoring positive and/or negative pressure changes.

Recently, non-invasive methods have been developed involving chemical sensors disposed inside the container. These sensors respond to changes in the carbon dioxide concentration by changing their color or by changing their fluorescence intensity. In known automated non-invasive blood culture systems, individual light sources, spectral excitation/emission filters, and photodetectors are arranged adjacent to each container. This results in station sensitivity variations from one container to the next. Therefore, extensive and time-consuming calibration procedures are required to operate such systems. In addition, flexible electrical cables are required to connect the individual sources and detectors with the rest of the instrument. With the large number of light sources, typically 240 or more per instrument, maintenance can become very cumbersome and expensive when individual sources start to fail.

In known colorimetric or fluorometric instruments, light emitting diodes ("LEDs") are used as the individual light sources. These sources have only a relatively low optical output power. Therefore, high photometric detection sensitivity is required to monitor the container sensor emissions. This results in additional and more complicated front-end electronics for each photodetector, increasing production cost. To reduce equipment cost and complexity, it has been proposed to use optical fibers at each container to feed the output light of an instrument's sensors to a central photodetector. A disadvantage to this approach is the need for arranging a large number of relatively long fibers of different length within the instrument.

It has also been proposed to introduce a culture medium and blood specimen into each sealable glass container having an optical sensing means and a barcode label. Arranging a large number of these containers radially on a rotating drum within an incubator and mounting sensor stations in the instrument at a predetermined distance from the drum so that during rotation of the drum each individual container is passing over a sensor station. In that type of system, the inner bottom of each container is covered with a fluorescent chemical sensor and a linear barcode label is attached to one side of each container. The containers are then arranged radially on the rotating drum within the incubator, with each container neck oriented towards the drum's axis and all the containers located in groups on disk-like segments with each container reaching only partially into the drum so that the barcode labels are accessible for scanning.

To load and unload this apparatus, however, the user must grasp each container at its base and feed it into the drum neck-first. In known automated non-invasive blood culture systems, containers are commonly transported to the automated blood culture apparatus in an upright orientation, therefore, each container must be grasped twice before loading. The need to grasp each container twice to load each container neck-first into the drum requires additional work. Because microbiology lab personnel are accustomed to grasping containers at the neck, there is a need to overcome the unusual situation of feeding blood culture containers into the system neck-first. In addition, the apparatus must be loaded a container at a time, which also is very time consuming. Finally, if the drum stops for the purpose of loading and unloading, only a portion of the containers are accessible at a time.

SUMMARY OF THE INVENTION

The present invention overcomes the above problems and comprises a compact blood culture apparatus for detecting biologically active agents in a large number of blood culture containers that is simple and can be produced at very low cost. The apparatus uses a turntable having a plurality of wells located in concentric circles around a central axis, with each well receiving and holding one of a plurality of sealable containers inserted base first.

According to the present invention, each container includes optical sensing means therein for sensing microorganisms and a bar code pattern for identification purposes. Prior to inserting each container into a well on the turntable, a culture medium and blood specimen are introduced into the container and the bar code is scanned to identify the container. Then, as the containers are rotated on the turntable they are exposed to conditions enabling a variety of metabolic, physical, and chemical changes to take place in the presence of microorganisms within the specimen and rotated by one or more sensor stations that monitor the optical sensing means in the container to determine whether there is microorganism growth occurring within the container.

Such an apparatus provides low system sensitivity variations from one container to the next and does not require electronic or optoelectronic components, electrical wires, or optical fibers on a moving rack. As a result of these several advantages, it provides long-term reliability during operation. In addition, the present invention allows lab personnel to grasp each container at its neck during loading and unloading, offers simultaneous access to a large number of containers during loading and unloading, and has a smaller footprint as compared to existing blood culture systems without any increase in height.

These and other aspects, features and advantages of the present invention will become apparent from the following detailed description, taken in conjunction with the accompanying drawings.

DETAILED DESCRIPTION

Figure 1:
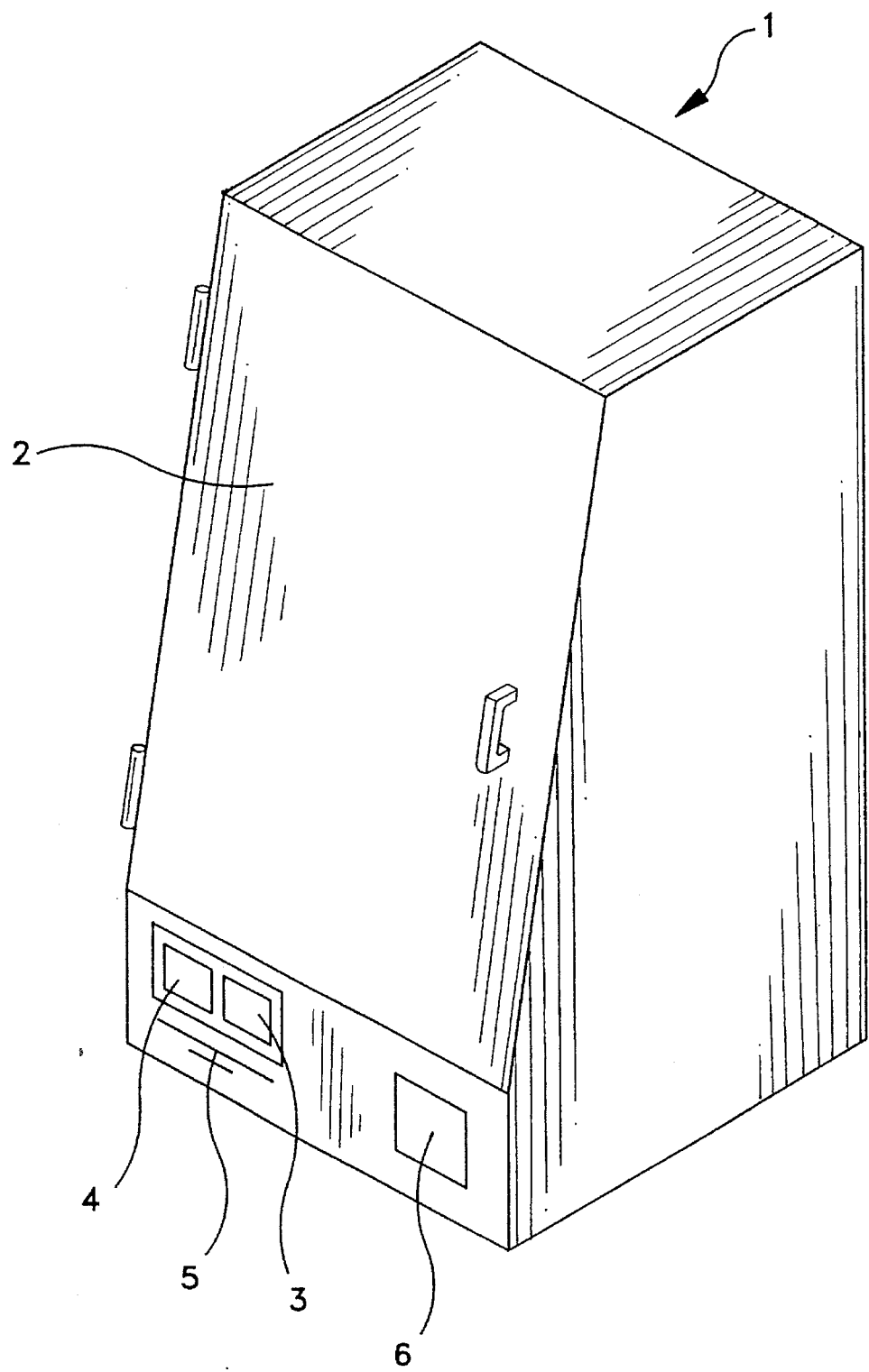
FIG. 1 shows a perspective view of a compact blood culture apparatus for the detection of microorganisms according to the present invention.
Figure 2:
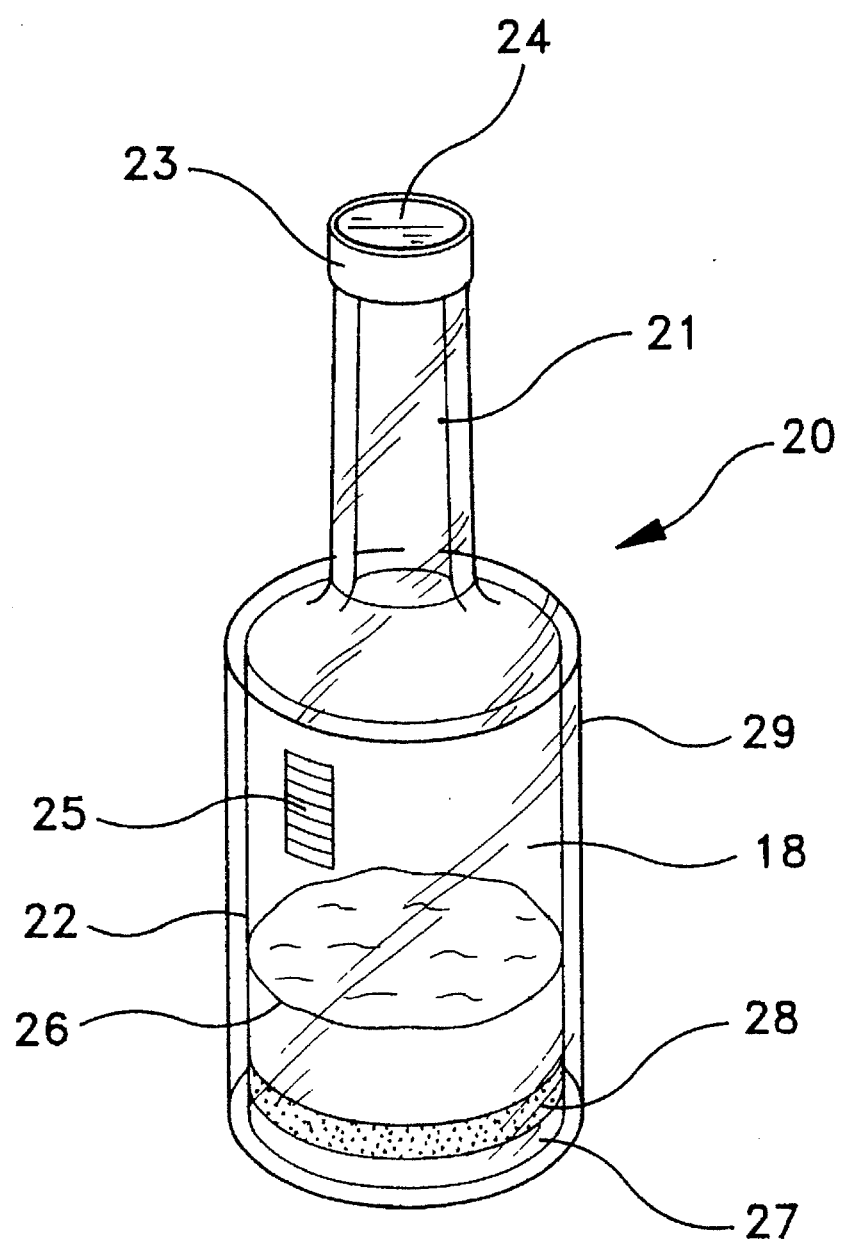
FIG. 2 shows a perspective view of a sealable container used in the apparatus shown in FIG. 1.

A perspective view of a compact blood culture apparatus 1 embodying the principles and concepts of the present invention is shown in FIG. 1. A plurality of containers 20, similar to the one shown in FIG. 2, are enclosed in the apparatus and protected from external environment and ambient light when under test by a hinged door 2 on the front of the apparatus. Heating means (not shown) are provided in the apparatus for incubating the containers at a temperature conducive to metabolism of microorganisms, e.g., 37° C., when door 2 is in a closed position.

A display 3 is provided on the from of the apparatus in FIG. 1 for indicating the operational status of the apparatus, and a control panel 4 provides a plurality of switches, i.e., for manually testing, turning apparatus 1 on and off, and controlling the overall operation of apparatus 1. A conventional computer disk drive 5 is provided on the front of apparatus 1 for loading and retrieving data and programs into and out of apparatus 1 and a bar code reader 6, located on the front of apparatus 1, is provided to scan a bar code label 25 on each container 20 and identify each container 20 being loaded into apparatus 1.

A perspective view of a preferred container 20 for use with the present invention is shown in FIG. 2. Container 20 includes a neck portion 21 and a base portion 22, with neck portion 21 having a smaller diameter than base portion 22. A cap 23 seals the open upper end of neck portion 21 and includes septum 24 that permits a needle to be inserted into container 20 for injecting a fluid specimen into container 20 and then reseals the open end of container 20 when the needle is withdrawn. Container 20 is shown as including a growth culture medium/blood mixture 26, which stimulates the growth of bacteria that may be in the fluid that is injected into container 20 when container 20 is incubated and agitated. In addition, it is preferable for each container 20 to contain a separate and distinct bar code label 25 on the outside of a sidewall 29 to provide efficient tracking of each container and minimize reporting errors.

In the embodiment being described, a fluorescence chemical sensor 27 is mounted at the bottom of base portion 22 for non-invasively monitoring the concentration of gases such as oxygen or $CO_2$ or such parameters as pH in container 20. As bacteria in the fluid specimen injected through septum 24 into container 20 grows in growth medium/blood mixture 26, bacteria metabolism generates $CO_2$. Therefore, the detection of $CO_2$ in container 20 by sensor 27 indicates that bacteria are growing within container 20. In addition, container 20 contains an optional resin medium 28 to absorb any antibiotics or drugs that may have been injected into the container with the specimen.

If the fluid specimen that is injected into each container 20 is blood, the apparatus according to the present invention provides a non-invasive blood culturing system that periodically and concurrently monitors, agitates and incubates the containers. Since each container 20 contains a fluorescence chemical sensor 27 that continuously monitors the blood culture in container 20, the blood culturing system based upon the below-described apparatus provides the earliest possible detection of bacterial growth in each container 20. In addition, the system provides a continuous source of periodic data concerning the growth of bacteria in the blood culture in each container 20 which can be stored and analyzed at a subsequent time. Therefore, the apparatus provides for the simultaneous agitation and incubation of all of the containers in a closed environment, so to provide an ideal environment for the growth of bacteria within each container.

Figure 3:
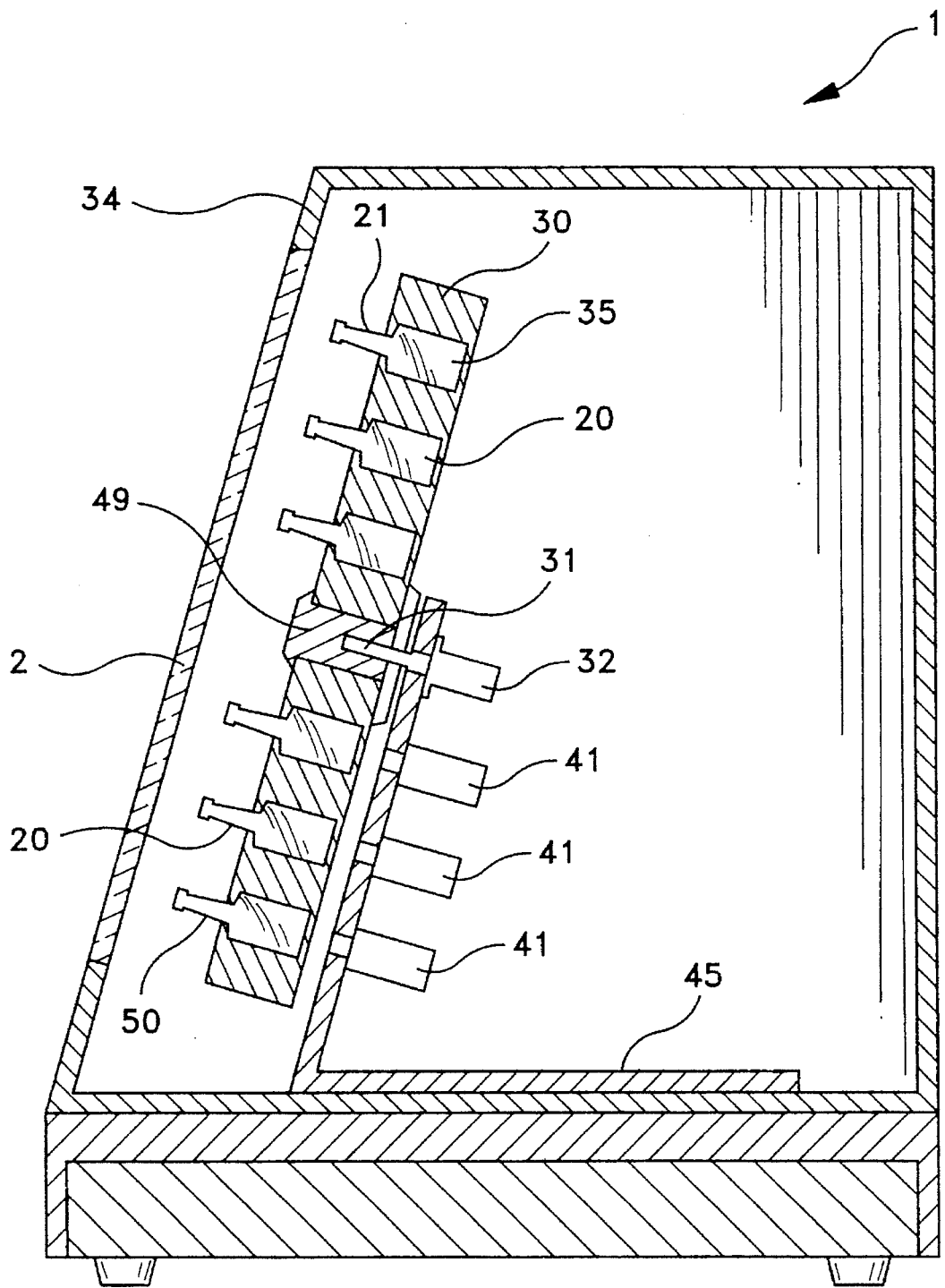
FIG. 3 shows a cross-sectional view of the apparatus shown in FIG. 1.
Figure 4:
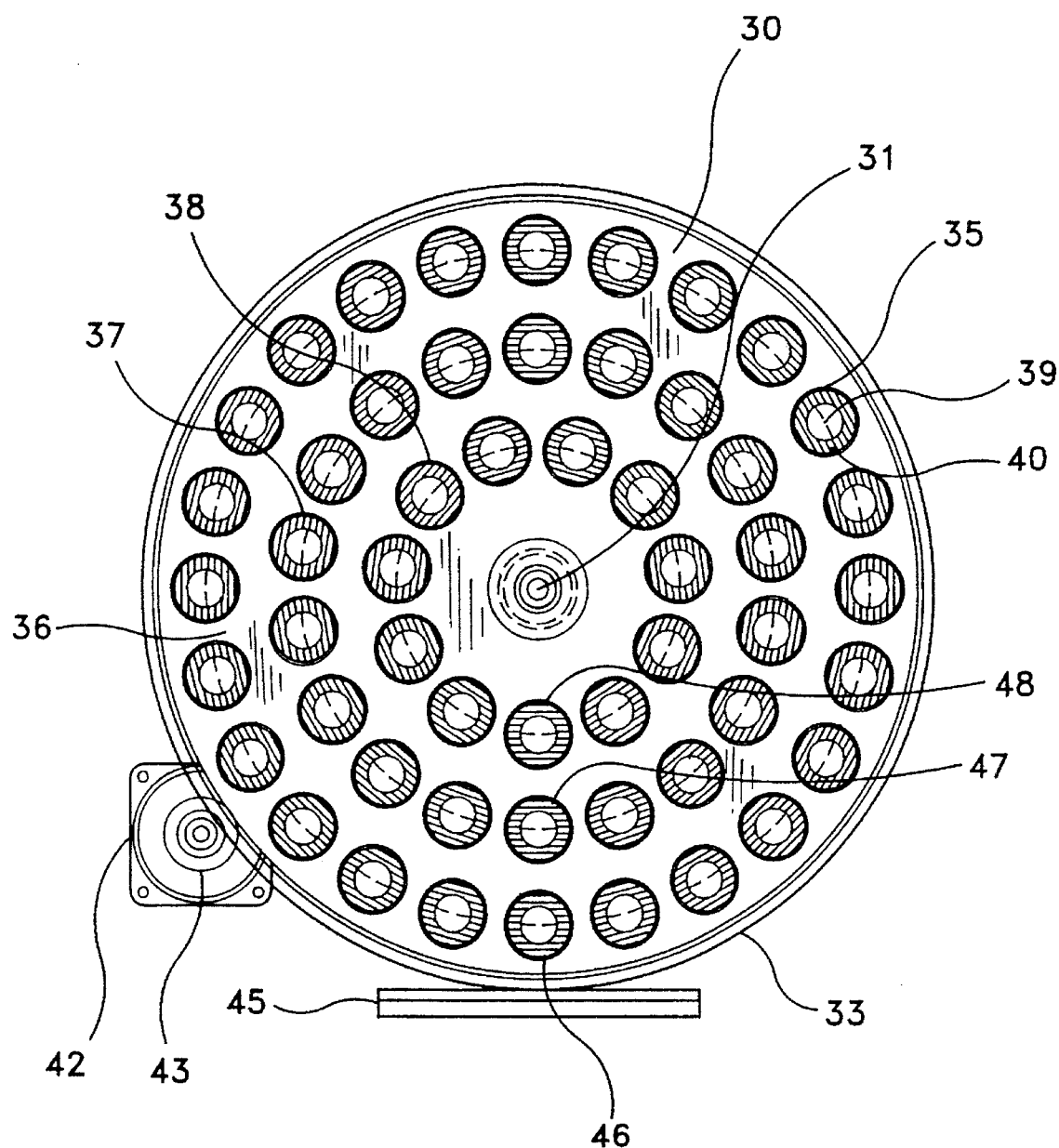
FIG. 4 shows an elevational plan view of the turntable in the apparatus shown in FIG. 3.

FIG. 3 is a cross-sectional view of apparatus 1, shown in FIG. 1, and shows a turntable 30 containing a plurality of wells 35 accessible from the front of turntable 30. As shown in FIG. 4, the plurality of wells 35 are arranged in three concentric circles 36, 37 and 38 and each well 35 is shaped to receive one container 20 base first. Each well 35 also includes an opening 39 in its base 40 to allow visible access to each fluorescence chemical sensor 27 from behind turntable 30. Turntable 30 is mounted on a shaft 3 ! that rotates in a bearing assembly 32 mounted on a mounting plate 45 within apparatus 1 and oriented so that containers 20 are oriented with their necks 21 toward door 2 on apparatus 1 and off-set from the horizontal plane. In such an arrangement, the force of gravity efficiently agitates medium/blood mixture 26 as turntable 30 rotates. Turntable 30 is also arranged within an incubator 34, shown in FIG. 3, to promote microorganism growth within containers 20. Of course, the present invention is not limited to an apparatus with the orientation shown in FIG. 3.

As shown in FIG. 4, rotation of turntable 30 is accomplished by a motor 42 that is connected to turntable 30 at its periphery 33 by a drive wheel 43. Of course, the arrangement shown in FIGS. 3 and 4 is merely exemplary, since other means for rotating turntable 30 could be used and still remain within the scope of the present invention.

A plurality of sensor stations 41 are secured to mounting assembly 45 in apparatus 1 at such a distance from turntable 30 that during its rotation individual wells 25 holding containers 20 pass over a sensor station 41, such that each fluorescence chemical sensor 27 is visible through opening 39 from behind turntable 30. In the preferred embodiment shown in FIG. 3, at least three sensor stations 41 are used, with one sensor station 41 testing each container 20 in a concentric circle 36, 37 or 38 for the concentration of one or more types of gas or such parameters as pH, as each container 20 in that circle passes over sensor station 41. Preferably, each sensor station 41 includes a light source that generates and directs light through opening 39 into well 35 towards the fluorescence chemical sensor 27 in each container 20. Sensor 27 then emanates differing quantities of light depending upon the amount of $CO_2$, oxygen or other gases or on the pH value detected by sensor 27. For example, the more gas or pH in container 20, the more light is emanated from sensor 27. The emitted light is then received by sensor station 41, which then transmits signal data to display 3 and disk drive 5, shown in FIG. 1, concerning the presence or absence of biologically active agents, such as bacteria, in each container 20. It should be understood, of course, that the use of a fluorescence chemical sensor is not required to practice the present invention, since other non-invasive means could be used to monitor gases within container 20, e.g., a scattered photon migration (SPM) technique. In addition, two or more detection principles could also be applied simultaneously, but may require more sensor stations 41 for each concentric circle 36, 37 and 38. Turntable 30 does not contain electronic or optoelectronic components, and no flexible electrical cables or optical fibers are required. Therefore, an apparatus according to the present invention can be produced at reduced cost compared to existing blood culture instruments. The turntable concept also allows for high density packaging.

Figure 5:
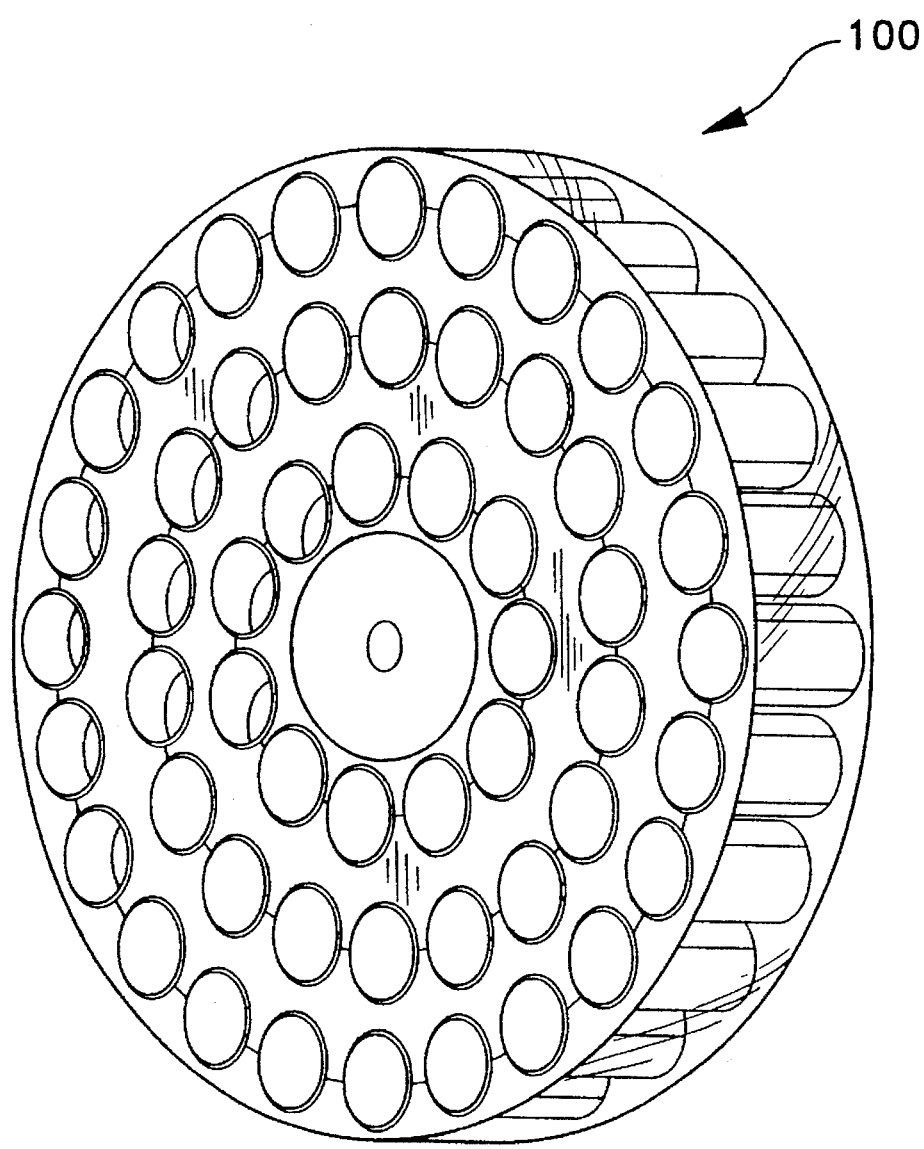
FIG. 5 shows a perspective view of an alternative turntable for use in an apparatus according to the present invention.

FIG. 4 shows an elevational plan view of a preferred turntable 30 for use in apparatus 1 and shows the outside concentric circle 36 having twenty-four (24) wells 35, the middle concentric circle 37 having eighteen (18) wells 35 and the inside concentric circle 38 having eleven (11) wells 35. One well 46, 47 and 48 in each concentric circle 36, 37 and 38, respectively, is reserved for a calibration vial or container 50 having a calibration material at its base that is used to calibrate the sensor station 41 assigned to that concentric circle 36, 37 or 38. Therefore, when turntable 30 is fully loaded it holds fifty (50) containers 20 and three calibration containers 50. Of course, other arrangements and numbers of wells 35 could be used and still fall within the scope of the present invention. For example, an alternate turntable 100 is shown in FIG. 5 that is concave rather than in a plane to provide additional agitation within each container 20 as it is rotated.

As described above, turntable 30 is rotated without stopping and fluorescence chemical sensors 27 are read "on the fly" as they rotate by one or more sensor stations 41. However, it is also within the scope of the present invention to stop turntable 30 when reading fluorescence chemical sensor 27 at a sensor station 41.

The present invention also overcomes the man-machine interface problem caused when containers had to be grasped at the bottom and fed into the system neck-first and offers simultaneous access to all fifty (50) containers during loading and unloading. An apparatus according to the present invention also has the advantage that, during operation, the containers never reach an upside-down orientation. This is an important safety feature in view of the potential for leaks in septum 24. In addition, an apparatus according to the present invention can be either equipped with an internal computer or can be connected to an external computer.

As has been mentioned already, turntable 30 does not contain electronic or optoelectronic components, and receives no electrical cables or optical fibers. This allows one to remove a loaded turntable after all chemical sensors 27 have been read. The turntable removed from the instrument could then be stored in a simple incubator on a slowly rotating shaft. In the meantime, a series of additional turntables 30, loaded with other containers 20, could be inserted into the instrument and read. This option would allow expansion of the effective throughput of the instrument significantly at minimum cost, if required. For easy removal and reinsertion, turntables 30 are equipped with a quick disconnect 49, as shown in FIG. 3.

The quick disconnect option of the present invention is, in particular, advantageous for remote hospitals that usually need only a small-capacity low-cost instrument. If, however, a seasonally related increase in the number of samples occurs, then the capacity can be expanded according to the specific situation. This option may also be useful to detect the presence of mycobacteria. In this case, the frequency of readings is much lower as compared to blood cultures. Therefore, it appears acceptable to insert each turntable once or twice per day into the instrument for read out.

In the foregoing discussion, it is to be understood that the above-described embodiments are simply illustrative of a preferred apparatus for practicing the present invention, and that other suitable variations and modifications could be made to these embodiments and still remain within the scope of the present invention.

What is claimed is:

1. A compact blood culture apparatus comprising:
   an incubator providing an environment for culturing,
   a turntable rotatable about an axis having a plurality of wells in a top surface for receiving a plurality of containers;
   a mechanism for rotating said turntable about said axis;
   at least one sensor station for detecting microorganism growth within each container as said turntable is rotated about said axis; and wherein each of said plurality of wells includes an opening through the bottom of said turntable and said turntable is positioned and arranged to provide visable access to said container by said at least one sensing station through said opening.

2. A compact blood culture apparatus according to claim 1, wherein said turntable includes a plurality of concentric rows of said plurality of wells, wherein each of said concentric rows corresponds to said at least one sensor station for detecting microorganism growth within said plurality of containers contained in said one row as each of said plurality of containers in said one row passes over said at least one sensor station.

3. A compact blood culture apparatus according to claim 1, wherein each of said plurality of conatiners includes a base and a neck and said base of each of said plurality of containers is received in one of said wells in said top surface of said turntable.

4. A compact blood culture apparatus according to claim 1, wherein said turntable is rotated by a motor attached to the periphery of said turntable.

5. A compact blood culture apparatus according to claim 1, wherein one of said plurality of wells contains a calibration container for calibrating said sensor station.

6. A compact blood culture apparatus according to claim 1, wherein said turntable is mounted on said axis using a quick disconnect that allows said turntable to be removed from said apparatus and replaced with another turntable.

7. A compact blood culture apparatus according to claim 1, wherein rotation of said turntable is periodically stopped by said mechanism so that each container is positioned at at least one sensor station for detecting microorganism growth within said container.

8. A compact blood culture apparatus according to claim 1, wherein each container passes by at least one sensor station for detecting microorganism growth within said container as said turntable is rotated about said axis by said mechanism.

* * * * *